United States Patent
Caughron et al.

[19]

[11] Patent Number: 5,837,040
[45] Date of Patent: Nov. 17, 1998

[54] ROOM AIR DECONTAMINATION DEVICE

[75] Inventors: James S. Caughron, Pendleton; John C. Williams, Knox, both of Ind.

[73] Assignee: International Decontamination Systems LLC, Pendleton, Ind.

[21] Appl. No.: 711,172

[22] Filed: Sep. 9, 1996

[51] Int. Cl.⁶ .................................................. B01D 50/00
[52] U.S. Cl. ...................... 96/224; 55/385.1; 55/385.2; 55/467; 55/480; 55/481; 55/506
[58] Field of Search ................... 95/273, 278; 55/279, 55/385.1, 385.2, 481, 506, 478, 480, 467, 318, 482, 485, 493, 504, 495; 454/187; 96/224

[56] References Cited

U.S. PATENT DOCUMENTS

| | | | |
|---|---|---|---|
| 2,626,083 | 2/1953 | Rense | 55/279 |
| 3,094,400 | 6/1963 | Blanton | 55/279 |
| 3,261,147 | 7/1966 | Allander | 55/279 |
| 3,659,874 | 5/1972 | Rendessy | 280/446 |
| 3,744,216 | 7/1973 | Halloran | 55/279 |
| 3,757,495 | 9/1973 | Sievers | 55/316 |
| 3,937,967 | 2/1976 | Steinitz | 55/318 |
| 4,019,508 | 4/1977 | Der Estephanian et al. | 128/142.7 |
| 4,124,361 | 11/1978 | Revell | 55/493 |
| 4,193,844 | 3/1980 | Neumann et al. | 55/504 |
| 4,198,221 | 4/1980 | Catlin et al. | 55/481 |
| 4,204,956 | 5/1980 | Flatow | 210/87 |
| 4,210,429 | 7/1980 | Golstein | 55/279 |
| 4,251,246 | 2/1981 | Andreychek | 55/481 |
| 4,334,896 | 6/1982 | Muller | 55/478 |
| 4,450,964 | 5/1984 | Wood | 55/481 |
| 4,520,072 | 5/1985 | Yoshino et al. | 428/403 |
| 4,521,234 | 6/1985 | Peebles, Jr. et al. | 55/481 |
| 4,566,251 | 1/1986 | Spisak et al. | 53/167 |
| 4,604,110 | 8/1986 | Frazier | 55/74 |
| 4,626,291 | 12/1986 | Natale | 134/21 |
| 4,665,617 | 5/1987 | Maier et al. | 30/374 |
| 4,774,974 | 10/1988 | Teter | 134/110 |
| 4,783,129 | 11/1988 | Jacobson | 312/1 |
| 4,812,700 | 3/1989 | Natale | 312/1 |
| 4,820,000 | 4/1989 | Jacobson | 312/1 |
| 4,862,009 | 8/1989 | King | 290/22 |
| 4,865,401 | 9/1989 | Jacobson | 312/1 |
| 4,871,559 | 10/1989 | Dunn et al. | 426/248 |
| 4,901,673 | 2/1990 | Overstreet | 119/77 |
| 4,910,942 | 3/1990 | Dunn et al. | 53/425 |
| 4,990,313 | 2/1991 | Pacosz | 55/279 |
| 4,995,914 | 2/1991 | Teter | 134/21 |

(List continued on next page.)

FOREIGN PATENT DOCUMENTS

| | | | |
|---|---|---|---|
| 634512 | 8/1936 | Germany | 55/506 |
| 3731045 | 3/1989 | Germany | 454/158 |
| 4216343 | 11/1993 | Germany | 454/158 |

*Primary Examiner*—Duane S. Smith
*Attorney, Agent, or Firm*—Woodard, Emhardt, Naughton, Moriarty & McNett

[57] ABSTRACT

Room air is pulled from an inlet into a pre-filter duct and moved therethrough and through a main filter duct to an outlet in the room or some other location. The flow path is through a pre-filter unit, blower, germicidal light unit, and HEPA or ULPA filter unit to the outlet. Each of the units is readily replaceable and is furnished with a bio bag. The ducts have access openings in the duct wall at the unit locations. The access openings have flanged collars, with removable covers thereon. For installation of a unit, the bio bag is opened and secured to the flange, followed by removal of the flange cover. Then the unit is installed in the duct, the cover re-installed on the flange, and the bag rolled up in place, still attached to the flange, and remains so during operation of the apparatus and during removal of the unit at the end of its useful life, and then is used to encapsulate the used unit for disposal of the unit, to protect the service personnel from exposure to contaminants. Pneumatic actuators are used to move the HEPA filter into position in the duct where it is gel-sealed against a knife edge at the inner end of the pre-filter duct. The ducts are inside a sound-insulated outer cabinet which has access doors adjacent flanged openings at each of the filter units.

15 Claims, 7 Drawing Sheets

U.S. PATENT DOCUMENTS

| | | | |
|---|---|---|---|
| 5,017,197 | 5/1991 | McGuire et al. | 55/385.2 |
| 5,029,518 | 7/1991 | Austin | 98/31 |
| 5,034,235 | 7/1991 | Dunn et al. | 426/238 |
| 5,039,316 | 8/1991 | Hunter et al. | 55/97 |
| 5,069,691 | 12/1991 | Travis et al. | 55/126 |
| 5,074,894 | 12/1991 | Nelson | 55/210 |
| 5,131,934 | 7/1992 | Patel | 55/385.1 |
| 5,147,242 | 9/1992 | Lowe, Jr. | 55/385.2 |
| 5,152,814 | 10/1992 | Nelson | 55/270 |
| 5,160,517 | 11/1992 | Hicks et al. | 155/385.1 |
| 5,185,015 | 2/1993 | Searle | 55/279 |
| 5,225,000 | 7/1993 | Fujii et al. | 134/1 |
| 5,225,167 | 7/1993 | Wetzel | 422/121 |
| 5,230,723 | 7/1993 | Travis et al. | 55/350 |
| 5,240,478 | 8/1993 | Messina | 95/273 |
| 5,301,051 | 4/1994 | Geller | 359/124 |
| 5,380,503 | 1/1995 | Fujii et al. | 422/243 |
| 5,433,763 | 7/1995 | Shagott et al. | 55/323 |
| 5,436,268 | 7/1995 | Ohama et al. | 514/514 |
| 5,453,049 | 9/1995 | Tillman, Jr. et al. | 454/228 |
| 5,493,123 | 2/1996 | Knollenberg et al. | 250/372 |
| 5,506,126 | 4/1996 | Seed et al. | 435/172.3 |
| 5,523,057 | 6/1996 | Mazzilli | 55/279 |

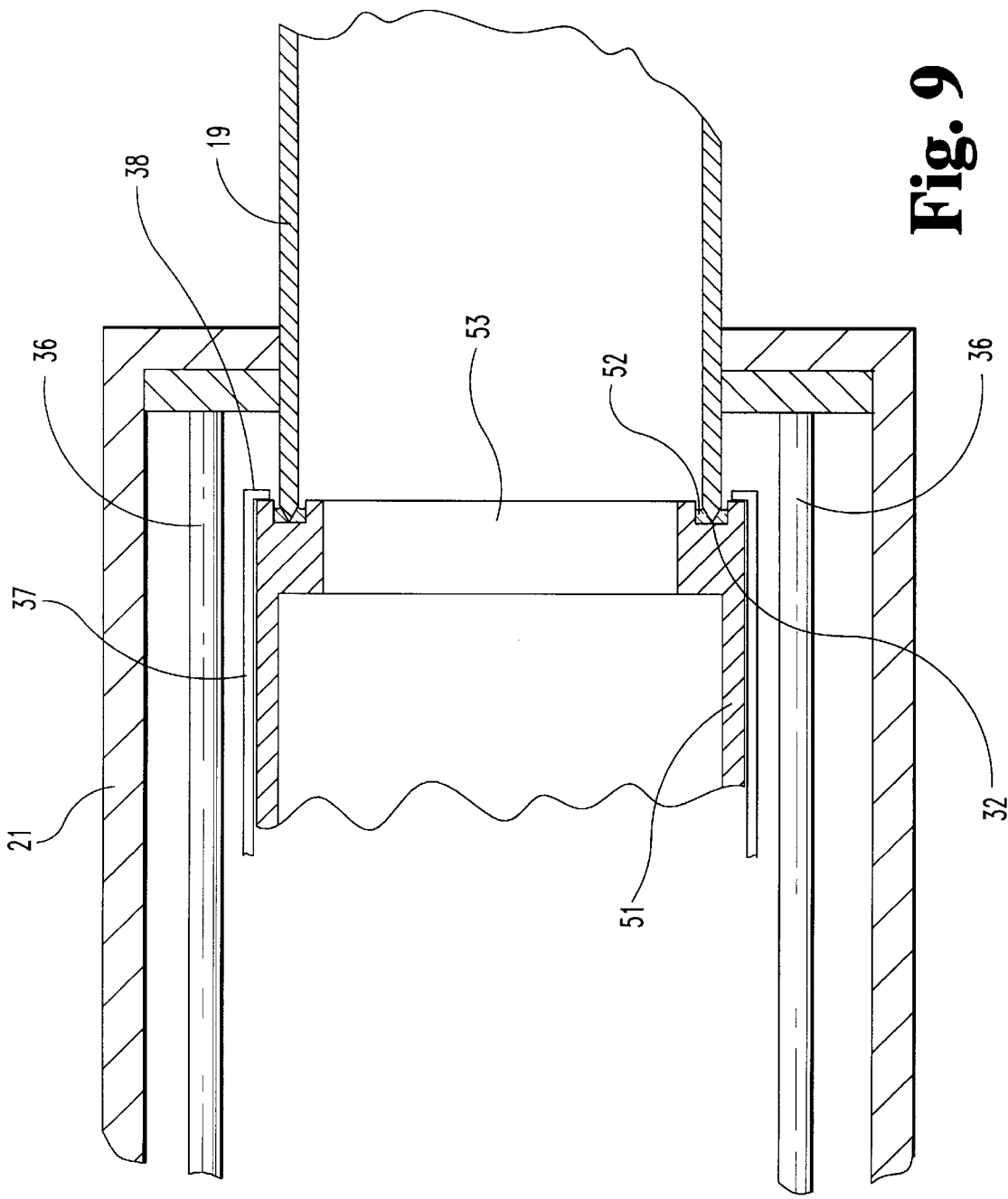

ROOM AIR DECONTAMINATION DEVICE

BACKGROUND OF THE INVENTION

1. Field of the Invention

This invention relates generally to environment control and more particularly to apparatus for removing and disinfecting impurities from room air.

2. Description of the Prior Art

It has been well known for many years to employ filters in air circulation systems in buildings. In recent years, more sophisticated arrangements for improving air quality in buildings have been developed. Some have been patented. For example, U.S. Pat. No. 5,453,049 issued to Tillman and Smith on Sep. 26, 1995 discloses an air purification or filtration device including a high efficiency particulate air (HEPA) filter or a low penetration air (ULPA) filter and a circulating fan within the housing to draw air through the filter and housing and exhaust air through the top of the housing for recirculation. It says that a germicidal ultraviolet light may be in the housing for additional air purification. The device is intended to be portable and located in the corner of a room. A device for wall mounting and which includes a HEPA filter and ultraviolet germicidal lamp is disclosed in U.S. Pat. No. 5,225,167 issued Jul. 6, 1993. An earlier effort is disclosed in U.S. Pat. No. 3,757,495 issued Sep. 11, 1973, which discloses a unit which can be either stationary or portable for recycling air within a room, filtering it, exposing it to a germicidal ultraviolet light and returning the purified air to the room. Other apparatus has been devised for the same purpose, so it should be understood that these are mentioned only as examples.

Although the direct problem of cleaning contaminated air has been addressed by these patentees and others, we are not aware of anyone addressing the need to facilitate maintenance of the equipment while, at the same time, protecting the maintenance workers from exposure to contaminants. The present invention is addressed to that need.

SUMMARY OF THE INVENTION

Described briefly, according to a typical embodiment of the present invention, an assembly which is easily provided in either a portable form, a stationary form, or can be incorporated in existing air circulation systems, includes a pre-filter duct and a main filter duct and a blower. The ducts establish a flow path from an inlet at one end of the pre-filter duct to an outlet at an opposite end of the main filter duct. A pre-filter unit is located immediately inside the inlet and upstream of the blower. A germicidal ultraviolet light unit is located in the pre-filter duct downstream of the blower. A main duct filter unit is located in the main filter duct. All three units are in replaceable cartridge form, including bio bag enclosures which may be replaced in the ducts. The main duct filter unit is fitted in a pneumatically powered carriage to drive an intake face gel seal against a knife edge at the inner end of the pre-filter duct to establish a seal. Access openings are provided in the duct walls at each unit location. Bio bag attachment flanges are mounted to the ducts at each of the unit access openings. Each flange has a cover removable into a bio bag for access to the unit in the duct for removal and replacement of the units without exposure to the surroundings. The ducts are mounted inside an outer cabinet which has access doors adjacent the flanged openings on the ducts, the cabinet having air intake and exhaust openings at opposite ends.

BRIEF DESCRIPTION OF THE DRAWINGS

FIG. 9 is an enlarged fragmentary view showing the engagement of the gel seal on a HEPA filter with the pre-filter duct end.

DESCRIPTION OF THE PREFERRED EMBODIMENT

Figure 1:
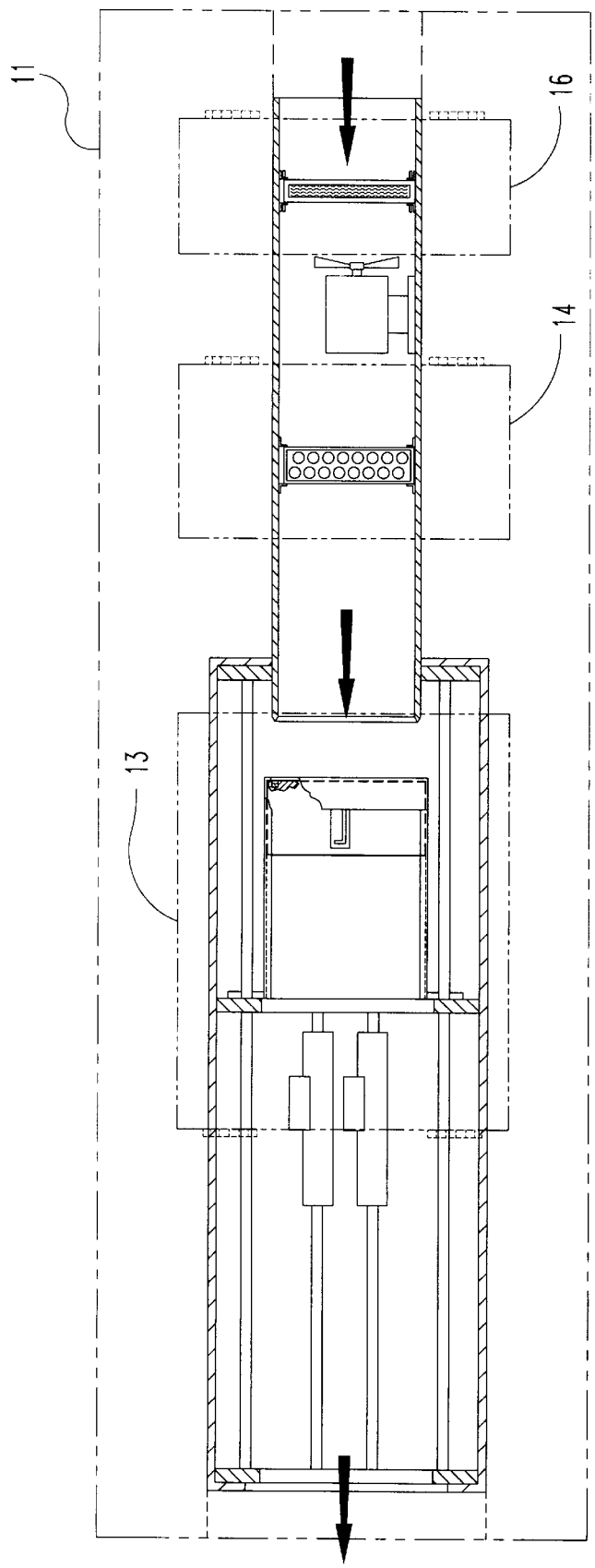
FIG. 1 is a front elevational view of a room air decontamination device according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
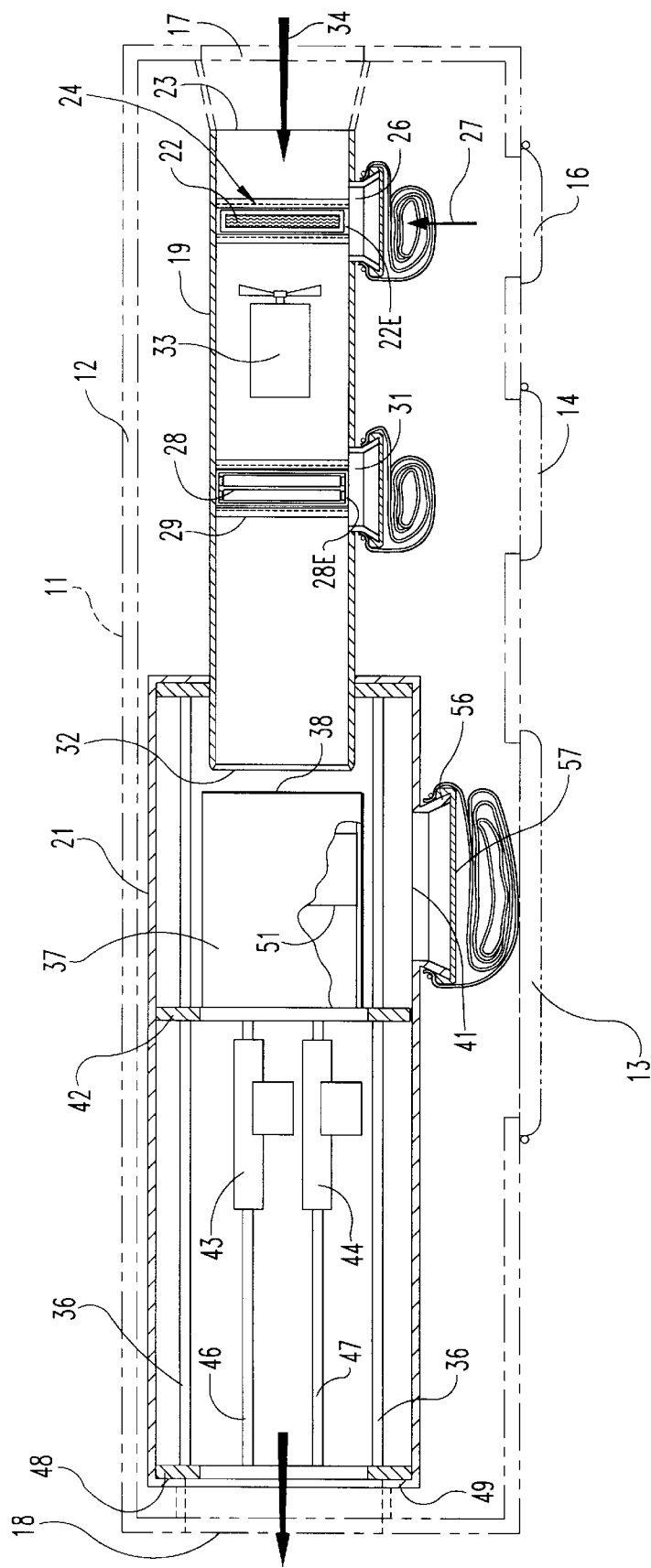
FIG. 2 is a top plan view.
Figure 3:
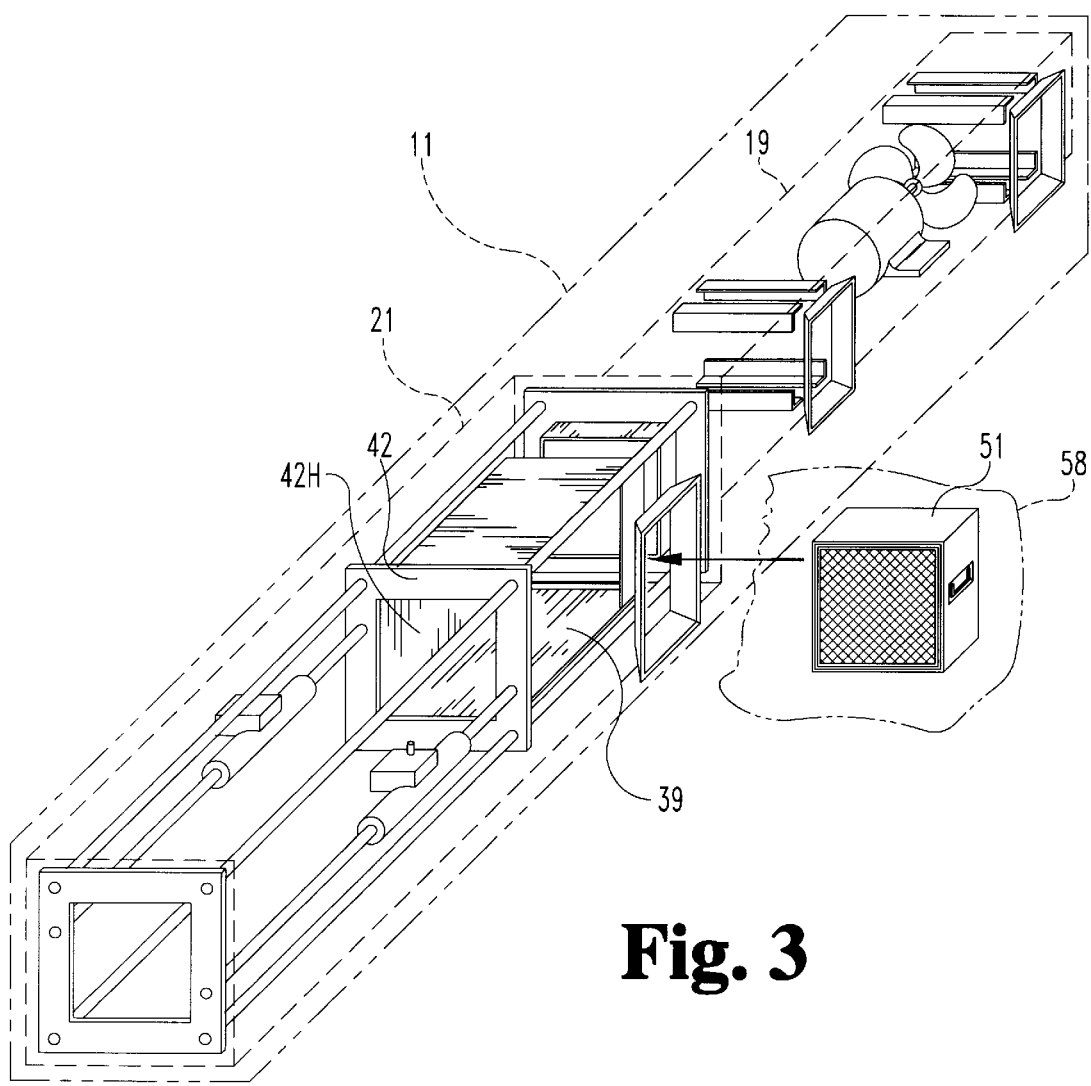
FIG. 3 is a perspective view.

Referring now to the drawings in detail, particularly FIGS. 1–3, the entire apparatus can be incorporated in an outer cabinet 11 shown in phantom because it can be of virtually any configuration, and mounted horizontally or vertically, and portable or stationary. As shown in FIG. 2, the cabinet may have a layer of insulation 12 between the outer face and inner wall for sound control. The cabinet has three access doors 13, 14 and 16 which are hinged to swing open horizontally for access to the filters inside. In the illustrated example, the outer cabinet has an air inlet opening 17 at the right-hand end, and an air outlet opening 18 at the left-hand end.

A pre-filter duct 19 is mounted in the cabinet and fixed and sealed to a main filter duct 21 also mounted inside the cabinet. Each of these ducts is typically rectangular in cross-section, as shown in FIG. 3.

A pre-filter unit 22 is provided near the inlet end 23 of the pre-filter duct. It is mounted in a frame 24 fixed in the duct and which facilitates reception of a filter through an opening 26 in the duct wall, whereby the filter can be slid into the frame in the direction of arrow 27 and removed in the opposite direction. Similarly, a germicidal ultraviolet lamp unit 28 is mounted in a frame 29 in duct 19 so such units can be installed and removed through opening 31 in the duct wall in the same way as filter 22. A blower 33 in the duct between the filter 22 and the germicidal unit 28 moves air through the assembly in the direction of arrow 34. Because of lower sound levels achievable and the ability to maintain higher air flow against resistance, a centrifugal blower with backward inclined blades is the blower of choice, and provided with a totally enclosed motor to facilitate decontamination without damage to the motor.

The main duct 21 has a set of four guide rods 36. These serve to mount and guide a filter carriage 37 which is generally closed but has a continuous lip open front end 38 and open side 39 for installation and removal of a filter unit. The side opening faces the wall opening 41 of the duct 21. The rear end of the carriage 37 is the platen 42 frame having four holes therein with bushings which slide on the guide rods 36. Pneumatic actuators 43 and 44 are connected to the platen 42 and mounted to piston rods 46 and 47 anchored to the frame 48 fixed in the duct 21 at the outlet end 49.

Each of the four walls of duct 19 has a knife edge at the inner end 32 of the duct. A HEPA filter 51 is received in carriage 37 and is immovable axially relative to the carriage. But, as shown in FIG. 9, it has an integral sealing gel ring in a recess 52 around the entrance end opening 53 and which, when the actuators 43 and 44 are actuated, is engaged with the knife edge 32 around the outlet end of the pre-filter duct 19 so as to provide a complete perimetrical seal between the duct 19 and the HEPA filter. Thus, the cylinders 43 and 44 are used to move the filter carriage and thereby the HEPA filter with it from the access position shown in FIGS. 1, 2 and 3 to the operating position shown in FIG. 9, where the filter is sealed to the pre-filter duct 19.

Each of the access openings 26, 31 and 41 in the ducts is provided with an entrance collar-flange unit such as 56. Since they all function in the same way, a description of one will suffice for all. Each has a cover 57 which can be snapped over the periphery of the flange to retain the cover in place. Other arrangements can be used if desired.

Figure 4:
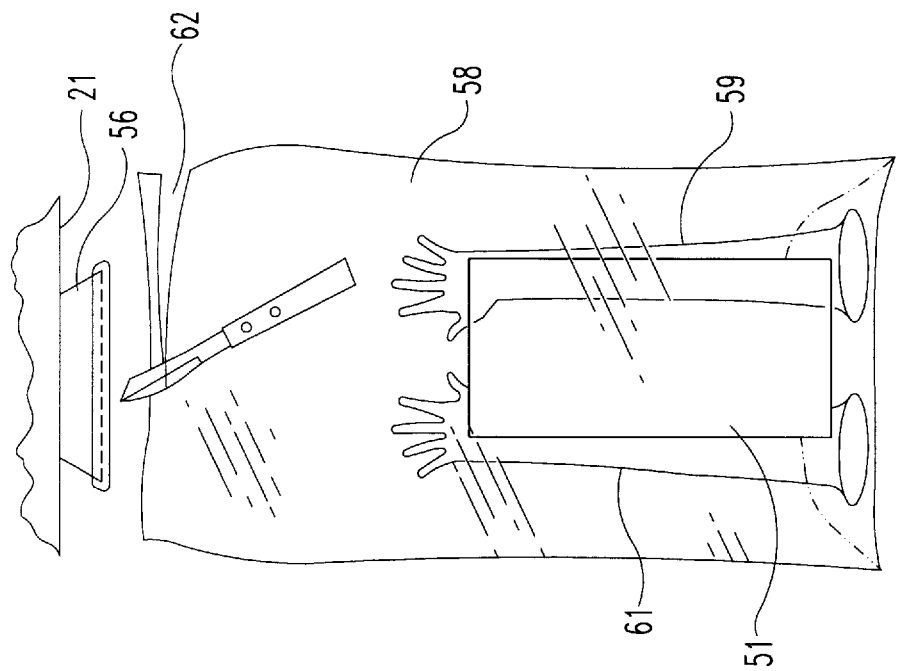
FIG. 4 is a fragmentary view illustrating a first step toward the installation of a new filter.
Figure 5:
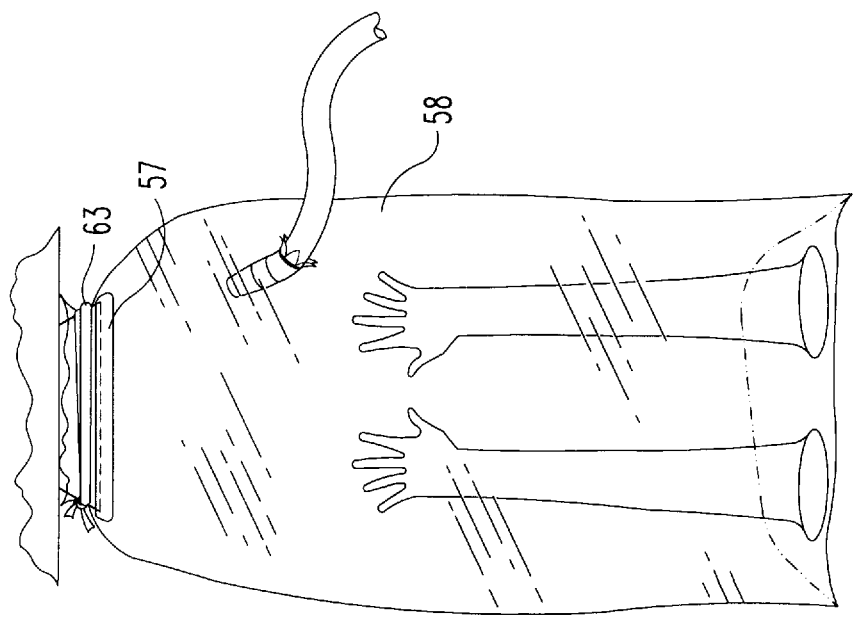
FIG. 5 illustrates a second step.
Figure 7:
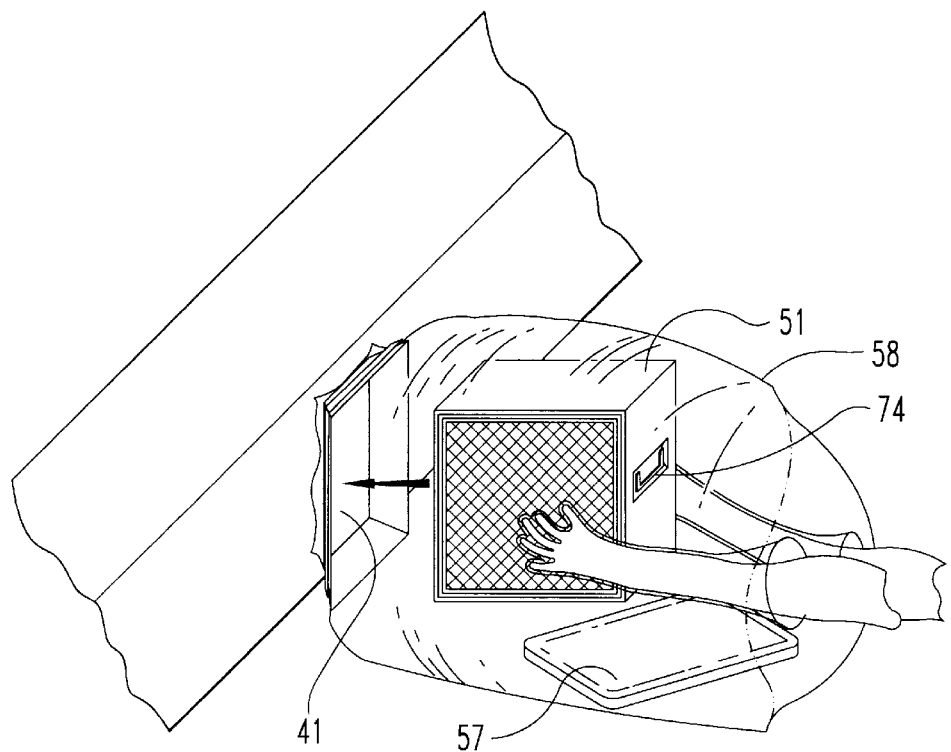
FIG. 7 illustrates a fourth step, actually installing the filter.
Figure 6:
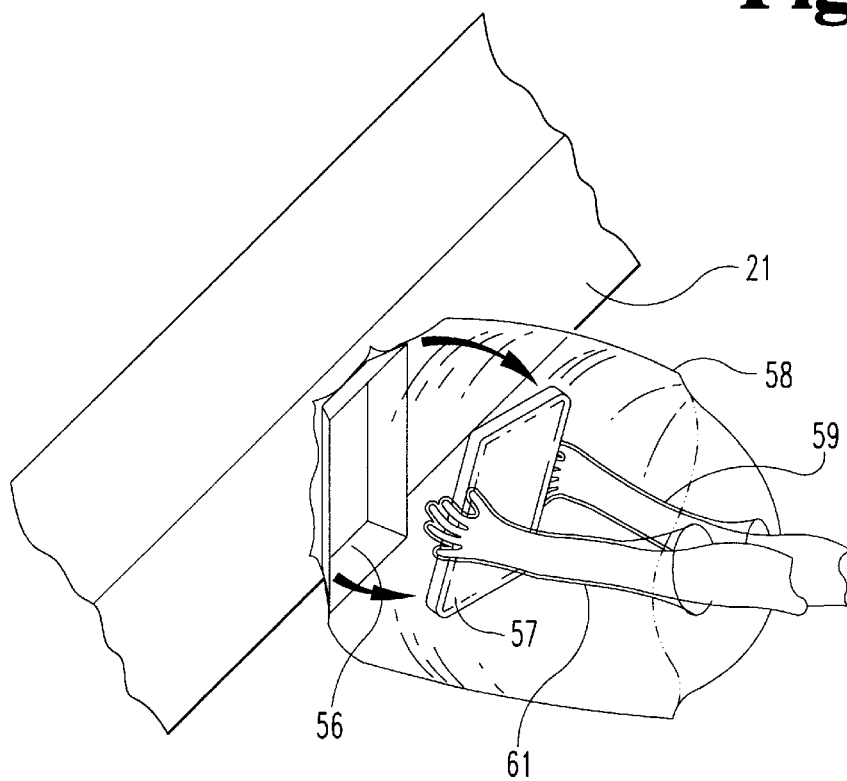
FIG. 6 illustrates a third step.

Referring now to FIG. 4, and wherein the proportions of the parts are not intended to be accurate, since it is only for purposes of description of the concept, a new HEPA filter 51 is supplied in a bio bag 58 of the type having built-in arm and hand receivers 59 and 61, such a bag sometimes referred to as a glove bag. To install the filter, the door 13 (FIG. 2) of the outer cabinet is opened. The upper end of the bio bag is cut open at 62 (FIG. 4). Then the cut open end is slipped over the flange 56 as in FIG. 5, for example, and tied and sealed onto the flange 56 by a garter or other form of tie 63. Then the maintenance person places hands in the gloves 59 and 61 and pulls the cover 57 off the flange into the bag. This step is illustrated in FIG. 6, but the filter 51 is omitted from the figure to avoid clutter in the drawing. Then (FIG. 7) the HEPA filter is pushed through the opening 41 and into the carriage 37 where it is fittingly received and snug on all sides so that the air passing into it will not bypass it but will instead go entirely through the filter and then through the hole 42H (FIG. 3) in platen 42. Then the closure cover 57 is re-installed on the flange 56. Then the portion of the now empty bag 58 hanging out through the outer cabinet door opening is rolled up to position (FIG. 2) inside the opening and taped or tied in the rolled up condition. Then the door 13 is closed. Then the pneumatic cylinders 43 and 44 are activated to drive the platen to the right so the sealing gel engages and is penetrated by the knife edge 32 around the perimeter of the pre-filter duct 19. The cylinders are then stopped at the appropriate predetermined location so the knife edges are well into the sealing gel but not necessarily touching the bottom of the perimetrical gel groove in the end of the filter cartridge.

Installation of the pre-filter unit 22 and the ultraviolet lamp unit 28 is accomplished in exactly the same way. In all three cases the bio bags in which the units are supplied may be attached initially to the outer end wall such as 22E for pre-filter 22 and 28E for the ultraviolet unit 28 to facilitate handling or keeping the bag in place with respect to the unit when the opposite end is cut open as in FIG. 4, prior to mounting on the respective flanges 26, 31 and 56.

When a filter is to be removed, the procedure is as follows, using the HEPA filter as an example. The pneumatic actuators 43 and 44 are reversed to return the carriage to the load-unload position shown in FIGS. 1, 2 and 3. Then the door 13 is opened. Then the bio bag is unrolled and the operator's hands inserted in the glove or gloves 59 and 61.

Figure 8:
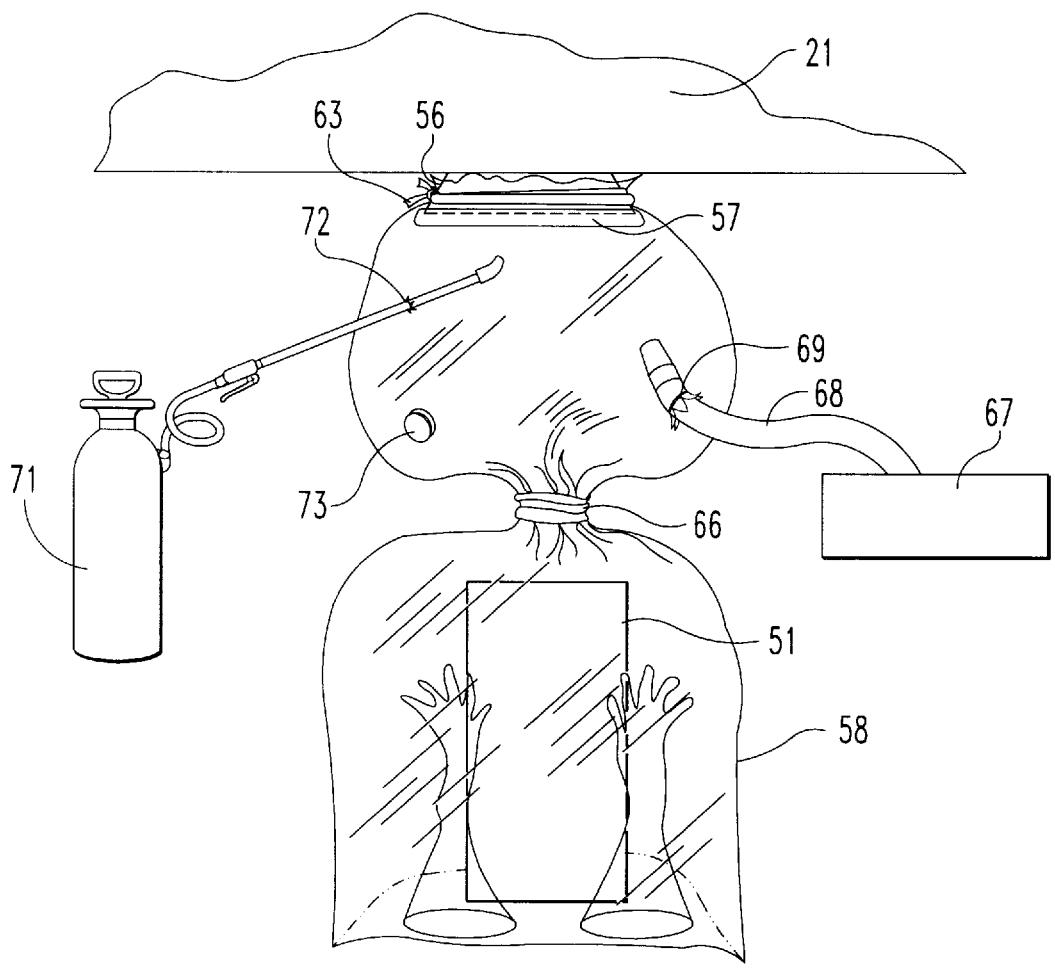
FIG. 8 illustrates a decontamination step following removal of a used filter.

Then the cover 57 is pulled off the flange 56. Then the HEPA filter is pulled out of the carriage 37 and into the bag as far as it will go into the outer end of the bag. Then the bag is twisted at its middle as shown in FIG. 8 and then tied at 66 to seal it closed at the location, with the dirty filter in the outer chamber and the cover 57 loose in the inner chamber. Then a HEPA vacuum machine 67 has its vacuum hose 68 inserted through a small hole punched at 69 in the bio bag portion attached to the flange 56 and turned on so as to pull any contaminated air from the inner chamber of the bag. Also, a pressure dispenser 71 containing germicidal solution has its nozzle portion inserted through another hole 72 punched in the bag to dispense germicidal solution throughout the inner chamber portion of the bag attached to the flange 56. This is done while the vacuum unit 67 is operating. An inhalation valve 73 is provided on the bio bag so work can be done without the bio bag compressing. The inhalation valve is a check valve which allows gas flow into the bag through the valve but prevents gas flow out of the bag through the valve. While this is done, the cover 57 which is still separate from the flange, can be treated directly with the germicidal solution. Then it is reinstalled on the flange as shown at 57 in FIG. 8. Then the vacuum hose 68, and the disinfectant tube 72 can be pulled from the bag and the holes taped shut. Then the garter or tie string 63 can be removed to enable removal of the open end of the bag from the flange. Then the open end is closed and tied and the bag with the HEPA filter in it is taken away for proper disposal. Then a new filter with its own bio bag can have its bag opened as described above with reference to FIG. 4 and the filter installed as described above. The same procedure is followed for removal of used pre-filter unit or a malfunctioning ultraviolet unit for replacement in the same manner as the HEPA filter is replaced.

As an example of the pre-filter 22, it employs three principles of filtration, namely: viscous impingement, straining, and interception. It can be constructed of 100% Dacron brand polyester fibers unaffected by moisture and humidity and occupying 100% of the face area of the filter. A non-toxic, non-allergenic, non-migrating tackifier is encapsulated between the last two layers of fiber, assuring a positive filter cake build-up and which does not support or feed bacteria or fungi growth. The pre-filter can be treated with an antimicrobial material. This filter is to be furnished in a bio bag of the above-type and, if desired, one edge of the bio bag can be attached to the filter at least until the time for placing the duct opening cover on the flange.

The ultraviolet disinfecting lamp unit includes the bag-in, bag-out UV bulb section 28 which provides the germicidal ultraviolet light for the destruction of bacteria and other micro-organisms in the air and on the face portion of the HEPA exposed to the bulb unit, and on the inner surface of the filter duct 19. One edge of the bulb unit can be attached to the bio bag for convenience, at least until time to place the flange cover on the flange.

The HEPA filter is preferably of one continuous sheet of highly efficient, water proof, graded density, microfiberglass paper individually tested for efficiency and pressure drop using a laser aerosol spectrometer or ASHREA DOP testing. The carriage for driving the HEPA filter cartridge end onto the knife blade provides a knife blade gel seal to prevent any contamination bypassing the HEPA filter where the filter engages the pre-filter duct. The HEPA filter may also be attached to its bio bag on one side, at least until the cover 57 is installed on flange 56.

The ducts are made of stainless steel with the inside surfaces highly polished to intensify the effect of the ultraviolet, and to facilitate decontamination.

Since various HEPA filters are available, it is preferred that for present purposes, the HEPA filter performance be 99.97% efficient at 0.3 micron particle size. Also, in those instances where a ULPA filter would be used instead of a HEPA filter, it is expected that a 99.99% efficiency be achieved at particle sizes of 0.1 micron. In addition to providing class 100 or 1000 for greater clean room standards on particle management efficiency, it should also be virtually bio contamination free.

In addition to providing room air cleaning and decontamination, this apparatus protects the maintenance and service personnel, by providing the bag-in, bag-out feature. It enables the worker to deal with the contaminated filters without ever coming into direct contact with the contamination. The original and replacement bag-in, bag-out (pre-filter or ultraviolet light or HEPA filter or ULPA filter) can be shipped and stored in a sealed bio bag to assure non-contamination. Attachment of an end of the bio bag to an edge of these units can be used if needed or desired to assist in orientation of the unit for installation into the ducts. After installation, detachment can be readily achieved without damage to the bag, as it is not contemplated that the attachment be rigid or permanent. A direct contact adhesive or intermediate tape can be easily used for this purpose.

During periods when the bio bag is attached to the flange on the duct for installation or removal of a unit, the HEPA vacuum can be applied to the bag to create a negative pressure in the bio bag. While this might not be as important upon installation of a new unit in a new duct, it is important upon removing a used unit and is desirable when installing a new unit to replace the previously used unit. Of course, it is desirable that filters, when installed in the filter frames, seat and seal appropriately against the walls of the duct and/or filter frame.

It is desirable that the pneumatic cylinders for moving the HEPA filter toward and away from the knife edge, be capable of advancing to and stopping in position accurately. Cylinders manufactured by SMC Pneumatics, Inc. have been found acceptable for this purpose. Valves and controls for operating these cylinders can be conventional and are well within the skill of the art.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the handle 74 in FIG. 7 might be used with a bag not having the hand receivers 59 and 61 in order to replace the filter.

What is claimed is:

1. Air decontamination apparatus comprising:
a cabinet having an inlet for contaminated air and an outlet for cleaned air;
a duct assembly inside the cabinet and having an air inlet associated with the cabinet inlet and having an outlet associated with the cabinet outlet for cleaned air;
a blower in the duct assembly and arranged to move air from the inlets, through the duct assembly and out through the outlets;
a first filter in the duct assembly upstream from the blower;
a germicidal light generator in the duct assembly downstream from the blower;
a final filter in the duct assembly and arranged to filter all of the air passing through the duct assembly to the outlets;
a bag associated with at least one of the filters to facilitate removal of the filter from the duct assembly without exposure of the filter to the environment outside the duct assembly;
wall openings in the duct assembly adjacent the filters;
flanges around the wall openings; and
closures on the flanges;
the bag associated with the one filter having an end secured around the flange at the opening adjacent the filter, with the closure inside the bag, whereby the closure can be removed from the end of the flange, and then the filter can be removed from the duct assembly into the bag, and then the closure can be re-installed on the flange without air communication between the interior of the duct assembly and the environment outside the duct assembly at the wall openings.

2. The apparatus of claim 1 and further comprising:
access openings in the cabinet adjacent the duct assembly wall openings; and
access doors on the cabinet at the access openings.

3. The apparatus of claim 2 and wherein:
the bag is rolled up while secured to the flange and is stored in the rolled-up configuration between the flange closure and the access door associated with the wall opening for the one filter.

4. The apparatus of claim 1 and further comprising:
a vacuum applicator and disinfectant applicator connected to the bag adjacent the flange, for removal of contaminants from the bag and for disinfecting the flange and closure.

5. The apparatus of claim 1 and further comprising:
a filter carriage in the duct assembly and receiving the one of the filters in the carriage; and
a carriage drive device coupled to the carriage to move the one filter into sealing engagement with a portion of the duck assembly.

6. The apparatus of claim 5 and wherein:
the duct assembly includes first and second ducts in series, each duct having a proximal end and a distal end, with portions of the ducts adjacent their proximal ends being sealed together and with the air inlet at the distal end of the first duct and the air outlet at the distal end of the second duct;
the proximal end of the first duct is a sealing knife edge;
the portion of the duct assembly sealingly engageable with the one filter is the sealing knife edge of the first duct;
the filter carriage is in the second duct;
the carriage drive device includes a fluid actuator in the second duct; and
the one filter in the carriage has an end sealable to the sealing knife edge of the first duct upon movement of the carriage into position sealingly engaging the one filter with the sealing edge.

7. The apparatus of claim 6 and wherein:
the one filter has an inlet face and has a sealing gel at the face receiving the knife edge therein to provide a perimetrical seal of the proximal end of the first duct to the one filter.

8. Air decontamination apparatus comprising:
a cabinet having an inlet for contaminated air and an outlet for cleaned air;
a duct assembly inside the cabinet and having an air inlet associated with the cabinet inlet and having an outlet associated with the cabinet outlet for cleaned air;

a blower in the duct assembly and arranged to move air from the inlets, through the duct assembly and out through the outlets;

a first filter in the duct assembly upstream from the blower;

a germicidal light generator in the duct assembly downstream from the blower;

a final filter in the duct assembly and arranged to filter all of the air passing through the duct assembly to the outlets;

a bag associated with at least one of the filters to facilitate removal of the filter from the duct assembly without exposure of the filter to the environment outside the duct assembly; and a bag associated with the light assembly to facilitate removal of the light assembly from the duct assembly without exposure of the light assembly to the environment outside the duct assembly.

9. Air decontamination apparatus comprising:

a duct assembly having an air inlet for air to be decontaminated and having an air outlet for decontaminated air;

a blower in the duct assembly and arranged to move air from the inlet, in a path through the duct assembly and out through the outlet;

a filter in the flow path;

a bag associated with the filter to facilitate removal of the filter from the duct assembly without exposure of the filter to the environment outside the duct assembly;

a wall opening in the duct assembly adjacent the filter;

a flange around the wall opening; and a closure on the flange;

the bag associated with the filter having an end secured around the flange whereby the closure can be removed from the end of the flange inside the bag, and then the filter can be removed from the duct assembly into the bag, and then the closure can be reinstalled on the flange without air communication between the interior of the duct assembly and the environment outside the duct assembly at the wall opening.

10. The apparatus of claim 9 and wherein:

the bag is rolled up at the flange closure.

11. The apparatus of claim 9 and further comprising:

a vacuum applicator and disinfectant applicator connected to the bag adjacent the flange, for removal of contaminants from the bag and for disinfecting the flange and closure.

12. Air decontamination apparatus comprising:

a duct assembly having an air inlet for air to be decontaminated and having an air outlet for decontaminated air;

a blower arranged to move air from the inlet, in a path through the duct assembly and out through the outlet;

an air treatment device in the flow path;

a bag associated with the device to facilitate removal of the device from the duct assembly without exposure of the device to the environment outside the duct assembly;

a wall opening in the duct assembly adjacent the device;

a bag mount and sealing surface around the opening;

a closure inside the bag and closing the opening;

the bag having an end secured around the sealing surface whereby the device can be removed from the duct assembly into the bag, without air communication between the interior of the duct assembly and the environment outside the duct assembly at the wall opening.

13. The apparatus of claim 12 and wherein:

the device is a filter.

14. The apparatus of claim 12 and wherein:

the device is a germicidal light.

15. The apparatus of claim 7 and wherein the one filter is the final filter, the apparatus further comprising:

a second bag associated with said first filter and having an end secured around the flange at the opening adjacent said first filter, with the closure inside the bag, whereby the closure can be removed from the end of said flange, and then the first filter can be removed from the duct assembly into the bag, and then the closure can be re-installed on the flange without air communication between the interior of the duct assembly and the environment outside the duct assembly at the wall opening adjacent the first filter;

a wall opening in the first duct adjacent the light generator, with a closure on the opening; and a third bag associated with the light generator and having an end secured around a flange at the opening adjacent the light generator, with the closure inside the bag, whereby the closure can be removed from the end of said flange, and then the light generator can be removed from the duct assembly into the bag, and then the closure can be re-installed on the flange without air communication between the interior of the duct assembly and the environment outside the duct assembly at the wall opening adjacent the light generator.

* * * * *